United States Patent [19]
Foldesy et al.

[11] Patent Number: 5,169,464
[45] Date of Patent: Dec. 8, 1992

[54] METHOD OF MAKING A CONDOM BY BLOW EXTRUSION

[75] Inventors: Robin G. Foldesy, Raleigh, N.C.; Robert G. Wheeler, Greenbank, Wash.

[73] Assignee: Family Health International, Durham, N.C.

[21] Appl. No.: 770,770

[22] Filed: Oct. 4, 1991

Related U.S. Application Data

[60] Continuation of Ser. No. 516,043, Apr. 27, 1990, abandoned, which is a division of Ser. No. 199,030, May 26, 1988, abandoned.

[51] Int. Cl.$^5$ .............................................. B29C 69/00
[52] U.S. Cl. ................................ 156/73.3; 156/73.1; 156/244.14; 156/244.17; 156/244.18; 156/251; 264/150; 264/151; 264/152; 264/564; 264/23
[58] Field of Search ............... 264/564, 565, 540, 572, 264/573, 150, 151, 163, 209.3, 152, 23; 425/532; 156/244.14, 244.17, 244.18, 251, 73.1, 73.3

[56] References Cited

U.S. PATENT DOCUMENTS

| | | | |
|---|---|---|---|
| 3,358,062 | 12/1967 | Lemelson | 264/540 |
| 3,433,862 | 3/1969 | Weber | 264/540 |
| 3,608,268 | 9/1971 | Lauritzen | 264/540 |
| 3,755,277 | 8/1973 | Toups | 264/540 |
| 3,963,801 | 6/1976 | Su | 264/564 |
| 4,123,589 | 10/1978 | Koriatzki et al. | 264/564 |
| 4,656,199 | 4/1987 | Niderellmann et al. | 264/176.1 |
| 4,810,451 | 3/1989 | Ermert et al. | 264/210.2 |
| 4,820,270 | 4/1989 | Hardcastle et al. | 264/176.1 |

FOREIGN PATENT DOCUMENTS

| | | | |
|---|---|---|---|
| 2728348 | 12/1977 | Fed. Rep. of Germany | 264/564 |
| 55-073517 | 6/1980 | Japan | 264/540 |

*Primary Examiner*—Jan H. Silbaugh
*Assistant Examiner*—Catherine Timm
*Attorney, Agent, or Firm*—Steven J. Hultquist

[57] ABSTRACT

A condom having a blow formed tubular main sheath portion, and a method for making the condom. Blow extrusion techniques of fabrication are described, together with the use of various thermoplastic materials of construction, including polyurethanes, polyether block amides, styrene-rubber-styrene block copolymers, ethylene-octene copolymers, and polyesters. The condom is made by blow extruding a tubular film of thermoplastic material to form a main sheath portion, severing the main sheath portion into one or more condom pieces, and sealing one end of each piece.

14 Claims, 1 Drawing Sheet

METHOD OF MAKING A CONDOM BY BLOW EXTRUSION

CROSS-REFERENCE TO RELATED APPLICATIONS

This is a continuation of U.S. application Ser. No. 07/516,043 filed Apr. 27, 1990, now abandoned, which in turn is a division of U.S. application Ser. No. 07/199,030 filed May 26, 1988, now abandoned.

BACKGROUND OF THE INVENTION

1. Field of the Invention

The present invention relates to a condom article and method for making the same.

2. Description of the Art

In recent years, there has been a significant increase in the incidence and spread of sexually transmitted diseases, and this phenomenon has in turn caused an increased use of condoms as a prophylatic measure to reduce the risk of infection and transmission of such diseases.

Among the reason for the increase in incidence and rate of transmission of sexually transmitted diseases (STD's) are the development of increasingly antibiotic-resistant strains of disease-causing organisms, e.g., those responsible for diseases such as syphillis and gonorrhea. Another factor has been the absence of any effective cure for acquired immunodeficiency syndrome (AIDS).

Recent disclosures by the Centers for Disease Control (Washington and Atlanta), and reports at the Third International AIDS Conference in Washington, D.C. in June, 1987, have focused international attention on the proliferation of acquired immunedeficiency syndrome (AIDS) in the general population, beyond the originally defined high-risk classification groups of homosexuals, bisexuals, intravenous drug users, and Haitain/African groups.

The diseases with which AIDS has been or is suspected to be linked include Pneumocystis carinii pneumonia, Kaposi's sarcoma, esophageal or bronchopulmonary candidiasis, extrapulmonary cryptococcosis, cytomegalovirus internal organ infection, disseminated Mycobacterium avium complex or M. kansasii infection, chronic herpes simplex ulceration, chronic cryptosporidiosis enteritis, toxoplasmosis of the brain, high-grade B-cell non-Hodgkin's lymphoma, disseminated histoplasmosis, chronic isosporiasis enteritis, and lymphoid interstitial pneumonia in children.

In a recent San Franciso cohort study reported in "AIDS: The Cost in Health and Lives," Selik, M. D. Richard M., et al, *The Internist*, April, 1987, p.p. 6 et seq., there was found to be, for every case of AIDS in the group studied, nine cases of other HIV-related morbidity. As also indicated in this article, cohort follow-up studies indicate that the proportion of HIV-infected persons who will ultimately develop AIDS ranges from 25% to 50% or more depending on the length of follow-up and the patient's clinical status at the beginning of the study. Mathematical modeling of this trend in reported AIDS cases has led to a projection that the cummulative total of AIDS cases will be 270,000 by 1991, and the number reported that year alone will be 74,000.

Against the foregoing background, and the recognition that condoms afford a safe, low cost, and generally reliable means for combating the spread of STD's, including AIDS, there has been an increased demand for condoms in developed, as well as developing countries, where some governments are distributing condoms to their citizens at no charge, to minimize the spread of STD's. As a result of the mass distribution of condom products, there is a need in the industry for the development of low cost, storage-stable condoms which are readily and simply produced in mass quantities, by methods and apparatus entailing low capital investment requirements.

Currently, most condoms are produced from a latex resin via a dipping process in which a cylindrical and rounded-end mold is dipped into a resin bath, so that the mold is coated with a thin layer of the latex material. The thickness of the latex coating on the mold is dependent on the viscosity of the latex, and the speed of extracting the mold from the latex bath. Similar latex dipping processes have been employed with suitably shaped molds to form tight-fitting gloves such as surgical gloves.

The above-described latex resin dipping process has been utilized for decades, and yields a generally satisfactory barrier product at reasonable cost.

With the recent spread of AIDS in the general population and the resurgence of condom usage in sexual activities, there has been interest in improving the strength and reliability characteristics of condoms, and of achieving improvements in manufacturing processes and economics, to further combat the spread of STD's generally, and AIDS specifically, as well as to provide a safe and reliable contraceptive means.

U.S. Pat. No. 4,576,156 issued Mar. 18, 1986 to Manfred F. Dyke discloses a condom formed of a thermoplastic polyurethane material, having a generally cylindrical configuration with an open proximal end and a closed distal end. The disclosed condom has a thickness of from about 0.01 millimeters, or less, to about 0.25 millimeters. The thermoplastic polyurethane employed to form the condom is disclosed as having: an average Shore A hardness of from about 50 to about 90; a tensile stress, at 100% of elongation, between about 300 and 1,000 psi; and a tensile stress, at 300% elongation, between about 800 and 3,000 psi. Suitable thermoplastic polyurethane species for manufacturing the condom include those set out at column 2, line 55 to column 3, line 10 of the Dyke patent, with polyether—or polyester—based urethane elastomers said to be preferred. In the manufacture of the thermoplastic polyurethane condom disclosed in the Dyke patent, a film of the polyurethane material, e.g., in the form of a 6-inch square, is heated to a temperature high enough to soften the polymer but low enough to avoid chemical degradation, preferably in a clamping frame, and at a temperature of about 400°-500° F. The heated film then is brought into contact with a preformed mandril to cause the film to assume the shape of the mandril, preferably with application of a vacuum to the system in order to bring about uniformity in wall thickness (column 3, lines 47-50 of the patent).

In an illustrative example described at column 4, lines 22-38 of the Dyke patent, an extruded film of Pellethane ® X5036-80AA polyurethane (The UpJohn Company, Kalamazoo, Mich.) is clamped on a clamping frame and heated at 460° F. for 180-200 seconds, following which vacuum is drawn on the film and the mandril moved downward into the film. Vacuum is shut off as the mandril moves into the film, then is applied at the base of the mandril after it has moved down into the film completely, such vacuum causing the film to pull down tightly and assume the shape of the mandril. After 30-100 seconds of vacuum forming in this manner, the vacuum is released, excess material at the base is cut off, and the film is partly rolled up onto itself for a distance of about 3 inches, on the 10-inch mandril, and then is dusted with powder and rolled up until it is removeable from the mandril.

Although the Dyke patent describes the condom product as having substantially uniform wall thickness, it will be recognized that the deformation of the thermoplastic polyurethane sheet with the heated mandril will inherently cause stretching and localized stresses and thinning, which in turn will cause non-uniformity of thickness over the entire areal extent of the condom article. Further, the nature of the deformation process using the preheated mandril is such that localized thermal stresses and temperature gradients will be developed, which may significantly adversely affect the strength and use characteristics of the condom product. In addition, the cutoff of excess material at the base of the mandril following the forming operation will result in significant wasteage of material and/or the necessity to rework such material in the process system. Finally, the use of small units of the polyurethane film, such as the 6-inch squares disclosed in the patent, entails significant disadvantages in terms of materials handling and the processing of the film stock, and may also entail significant material wasteage and/or reworking of material.

European patent application 0 147 072 published Jul. 3, 1985 in the names of Robert A. Taller, et al, discloses a process for making a polyurethane condom with a uniform thickness of from about 1.5 to about 4 mils. A heat cured polyurethane prepolymer solvent solution is employed into which a mold is dipped and withdrawn for heat curing on the mold. The polyurethane prepolymer which is employed in the dipping medium is a prepolymer which is the reaction product of a polyisocyanate with at least one long chain polyol. The polyol is amorphous at room temperature, has an average molecular weight of from about 500 to about 5,000, a hydroxy number of from 225 to about 22.4, and a NCO-/OH ratio of from about 0.95:1 to about 1.1:1.

The above-described process suffers the deficiencies inherent in all resin bath dipping methods for forming condoms, including slow processing times on a unit product basis, so that many dipping systems must be provided and concurrently operated to achieve high volume production.

For example, the European application states at page 7, line 18, that the condom mold may be dipped into and withdrawn from the polyurethane solution at a rate of about 16 to about 90 centimeters per minute; lines 25-27 at the same page of this application indicate that the dwell time of the condom form in the polyurethane prepolymer solution is on the order of from about 20 to about 70 seconds.

Once the mold is withdrawn from the solution, the polyurethane film deposited on the dipped form is air dried and then cured at elevated temperature, e.g., between about 130° C. and about 175° C., for about 20 to about 40 minutes, as disclosed at page 7, lines 33-35 of the application.

The polyurethanes employed in the process of the European patent application are segmented block copolymers constituted by alternating sequences of hard rigid segments and soft, flexible segments, in which the hard segment and the degree of crosslinking are balanced within the ranges of approximately 14-25 percent hard segment and approximately 5,000-30,000 molecular weight per cross link. The application states that the polyurethane polymers employed in the disclosed process provide a Shore A durometer hardness of about 35 to 60. Page 10, lines 19-22 of the application state that representative polyurethane polymers comprise from about 13% to about 23% isocyanate, from about 70% to about 84% long chain diol, and from about 0.75% to about 6% of a crosslinker.

A further disadvantage of the process of this European application is that the polyurethane prepolymer is utilized in solvent solution. Methylene chloride is disclosed as particularly convenient in such usage. The patent application discloses at page 15, lines 35-38 that the resin solution is maintained at a temperature between about 15° and about 25° C. to control viscosity and help prevent evaporation of the volatile solvent. Accordingly, the resin solution and the condom forms must be maintained at a low temperature to minimize loss of volatile solvent from the dip coating system.

It is accordingly an object of the present invention to provide an improved condom which is readily, simply, and inexpensively formed.

It is another object of the invention to provide a method for forming a condom of such type, which facilitates mass production of the condom.

Other objects and advantages of the present invention will be more fully apparent from the ensuing disclosure and appended claims.

SUMMARY OF THE INVENTION

The present invention relates to a novel condom comprising a tubular main sheath portion, closed at a distal end and open at a proximal end thereof.

Such condom be for example be formed of a thermoplastic elastomeric material or a suitable polymeric non-elastomeric material, and may advantageously be made by a process including blown film formation of the tubular main sheath portion.

In one preferred aspect, the present invention relates to a condom comprising a blown film tubular main sheath portion formed of a polyurethane material, e.g., a polyester-based polyurethane, having a specific gravity of from about 1.15 to about 1.25, a Shore A hardness of from about 80 to 95, a break tensile stress of from about 4500 to about 6,000 psi, a tensile stress at 50% elongation of from about 720 to about 2400 psi, an ultimate elongation of from about 450% to about 600%, a flexural modulus of from about 4,000 to about 37,000 psi, and a tear strength of from about 500 to about 1,000 pli.

In another preferred aspect, the present invention relates to a condom comprising a blown film tubular main sheath portion formed of a multiblock rubber-based copolymer material, e.g., a multiblock rubber-based copolymer material having a Shore A hardness from about 25 to about 100, a tensile strength of from about 500 to about 4500, a 300% modulus of from about 120 to about 1,000 psi, and an ultimate elongation of from about 200 to about 1400%.

In still another aspect, the present invention relates to a method of making a condom, comprising the steps of:
(a) blow forming a tubular film of a thermoplastic material; and
(b) sealing one end of said tubular film.

The blow forming step in the method described in the preceding paragraph may comprise blow extrusion forming, or alternatively blow molding, of the tubular film article.

Other aspects and features of the invention will be more fully apparent from the ensuing disclosure and appended claims.

DETAILED DESCRIPTION OF THE INVENTION, AND PREFERRED EMBODIMENTS THEREOF

The condom article of the present invention is of a general type having a tubular main sheath portion, closed at a distal end and open at a proximal end thereof.

Figure 1:
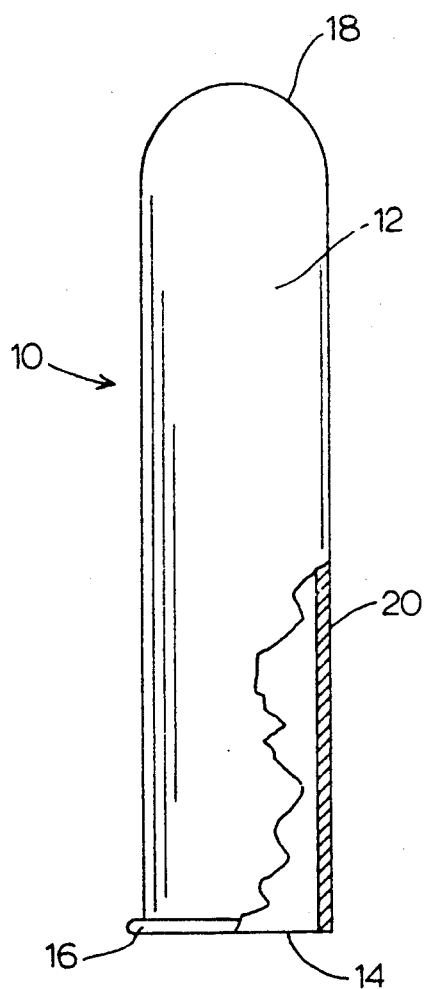
FIG. 1 is a partial sectional, elevational view of an illustrative condom according to one embodiment of the present invention.
Figure 2:
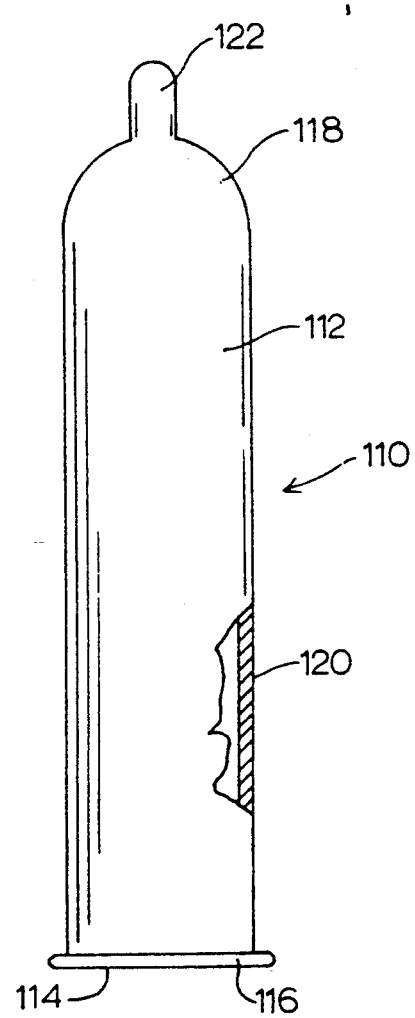
FIG. 2 is a partial sectional, elevational view of an illustrative condom according to another embodiment of the present invention.

Illustrative condom articles of such type are shown in FIGS. 1 and 2 hereof.

With reference to FIG. 1, there is shown a condom 10 comprising a tubular main sheath portion 12. The condom has an open proximal end 14, which as shown, may be circumferentially bounded by retaining ring 16. The condom is closed at its distal end 18.

FIG. 2 shows a condom of generally corresponding construction, wherein all elements analogous to those of the FIG. 1 condom are identified by corresponding reference numerals to which 100 has been added. The FIG. 2 condom differs from that shown in FIG. 1, however, by the addition of a distal tip reservoir 122 at the distal end 118 of the condom, for retention of ejaculate during use of the condom.

The condom of the present invention may advantageously be formed by blow forming the tubular main sheath portion of the condom from a suitable thermoplastic material. As used herein, the term "blow forming" is intended to be broadly construed to include (1) blow extrusion forming, in which a tubular film of a thermoplastic material is extruded and a pressurized fluid introduced in its interior, typically an air "bubble," whose pressure and flow rate determines the dimensional characteristics of the blown tubular film, and (2) blow molding, in which a tube of heated thermoplastic material is passed into an enclosing mold where a pressurized gas inside the tubular film expands the film into contact with the interior surfaces of the mold.

Irrespective of the specific type of blow formation technique employed to form the tubular main sheath portion of the condom article of the invention, the diameter of the tubular main sheath portion should be of a size commensurate with its intended use as a barrier means overfitting a male penis.

The condom articles of the invention may be of generally cylindrical shape, as in the illustrative embodiments of FIGS. 1 and 2 described hereinabove. Alternatively, it may be suitable in some instances to utilize the condom of the present invention in the form of a baggy-type penile enclosure which is wrapped about the penis for use, and retained in relatively looser configuration on the penis than are the condom articles shown in FIGS. 1 and 2, which are of a type closely overfitting the penis, and rolled or pulled onto the penis for use.

Thus, the specific structure of the condom article of the present invention may be widely varied, depending on the mode of application intended, and the specific materials of construction employed.

The materials useful for forming the condom articles of the present invention may variously include thermoplastic materials such as elastomeric thermoplastic materials, as well as non-elastomeric materials such as olefinic homopolymers and copolymers, e.g., ultra-low density polyethylene.

As used herein, the term "elastomeric" in reference to thermoplastic materials useful for forming condom articles in accordance with the present invention, means a material which subsequent to elongation thereof under an applied tensional force, regains at least a significant portion of its original dimensional characteristics when the applied tensional force is released.

Illustrative of thermoplastic elastomeric materials which may find utility in the broad practice of the present invention are: polyurethane materials, as for example the polyester-based polyurethane material commercially available from Mobay Corporation (Plastics and Rubber Division, Pittsburgh, Penn.) under the trademark Texin ®; polyester elastomers, such as the block copolymers of polybutylene terephthalate and long-chain polyether glycols, which are available commercially from E. I. Du Pont de Nemours and Company, Inc. (Polymer Products Department, Engineering Polymers Division, Wilmington, Del.) under the trademark HYTREL ®; polyether block amides, such as those commercially available from Atochem, Inc. (Glennrock, N.J.) under the trademark Pebax ®; multiblock rubber-based copolymers, particularly those in which the rubber block component is based on butadiene, isoprene, or ethylene/butylene, such as the multiblock rubber-based copolymers commercially available from Shell Chemical Company (Houston, Tex.) under the trademark Kraton ®; ethylene-octene copolymers such as those commercially available from The Dow Chemical Company (Midland, Mich.) under the trademark ATTANE TM; as well as any other suitable homopolymers and copolymers, and mixtures, alloys, and composites thereof.

Among the foregoing materials, polyester-based polyurethanes, and multiblock rubber-based copolymers are most particularly preferred.

The composition of multiblock rubber-based copolymers employed as materials of construction for the condom articles of the present invention may be varied widely, it being understood that the non-rubber repeating units of the copolymer may be derived from any suitable monomer(s), as for example, (meth)acrylate esters, such as methyl methacrylate, cyclohexylmethacrylate, etc.; vinyl arylenes, such as styrene; etc.

In general, the non-rubber blocks in the multiblock rubber-based copolymer preferably are derived from monomer(s) which are non-elastomeric in character, so that "soft" rubber blocks and "hard" non-elastomeric blocks are provided in the multiblock copolymer. Such hard blocks may suitably be derived from monomers having a glass transition temperature ($T_g$) of at least about 50° C., with styrene being generally preferred. The rubber block of such multiblock copolymers may be formed of repeating units derived from synthetic rubbers such as butadiene, isoprene, ethylene/butylene, etc., with butadiene and ethylene/butylene elastomeric blocks generally being preferred.

The most preferred multiblock rubber-based copolymers are those having an A-B-A structure comprising polystyrene endblocks and an elastomeric midblock.

Illustrative multiblock butadiene-based copolymers which may be usefully employed in the broad practice of the present invention include those variously described in U.S. Pat. Nos. 3,297,793; 3,595,942; 3,402,159; 3,842,029; and 3,694,523, the disclosures of which hereby are incorporated by reference herein. Various multiblock butadiene-styrene copolymers may be usefully employed to form the condom of the present invention, such as the aforementioned triblock ethylene-butadiene-styrene copolymers commercially available under the trademark Kraton TM from Shell Chemical Company (Houston, Tex.) and small block butadiene-styrene copolymers commercialized by Firestone Synthetic Rubber & Latex Company (Akron, Ohio) under the trademark Stereon ®.

In the general use of a multiblock rubber-based copolymer as the material of construction for the condom article of the present invention, the copolymer material preferably is characterized by the following physical properties: a Shore A hardness of from about 25 to about 100; a tensile strength of from about 500 to about 4500; a 300% modulus of from about 120 to about 1,000 psi; and an ultimate elongation of from about 200 to about 1400%.

With reference to the use of polyurethanes as materials of construction for the condom of the present invention, preferred material characteristics include: a specific gravity of from about 1.15 to about 1.25, a Shore A hardness from about 80 to about 95, a break tensile stress from about 4500 to about 6,000 psi; a tensile stress at 50% elongation of from about 720 to about 2400 psi, an ultimate elongation of from about 450% to about 600%, a flexural modulus of from about 4,000 to about 37,000 psi, and a tear strength of from about 500 to about 1,000 pli.

It will be recognized that processing conditions and apparatus may be varied widely in blow forming the tubular main sheath portions of condoms in accordance with the present invention, depending on the specific thermoplastic material employed in the blow forming operation, the volumetric space requirements of the process system, the method and apparatus employed for closure of the distal end of the tubular main sheath portion to form the finished condom structure, etc. The choice of specific processing conditions, materials, and the like may readily be determined for a given product application without undue experimentation, by those skilled in the art.

In blow extrusion forming of the main sheath portion of the condom, by way of example, the temperatures over a three-zone extruder may illustratively range from about 300° to about 380° Fahrenheit for a polyester-based polyurethane material or a multiblock butadiene-based styrene copolymer, while the temperature range in the same extruder for an ultra low density ethylene-octene copolymer or a polyether block amide may range from about 400° to about 450° F.; associated therewith are blow pressures which may range from 1 to 12 ounces per square inch of blown film, depending on the specific material employed.

When blow extrusion is utilized as the method for blow forming the tubular main sheath portion of the condom, the resulting tubular article has two open ends, and one of such open ends is sealingly closed to form the final condom article. The end closure operation may be carried out in any suitable manner, and preferably is automated so as to accommodate high speed manufacture of the condom article in high volume. Thus, the tubular body formed by blow extrusion may concurrently be sealed and severed at regular intervals along its length, to accommodate continuous processing.

The closure of the blow extruded tubular main sheath portion preferably is carried out by heat sealing, as is advantageous from the standpoint of thermoplastic materials being employed to form the condom.

The specific method of closure will depend largely on the specific material of construction employed for the tubular sheath portion of the condom, as well as its thickness. The wall thickness of the condom article may vary widely, but preferably is on the order of from about 0.05 to about 0.25 millimeter.

With such low thicknesses, it is important that the sealing method not produce differential stresses or other material deficiencies in the tubular main sheath in the vicinity of the distal end seal. Accordingly, when heat sealing is employed as a closure technique for forming the enclosed distal end of the condom, thermal impulse heat sealing is highly preferred, since it can initiate the sealing process at low temperature, with the material to be sealed thereafter quickly rising to the desired high sealing temperature, and then quickly returning to ambient temperature. Thus, rapid sealing of a localized region is effected, in a manner which prevents nearby regions of the film being sealed from experiencing substantial temperature changes, such as might otherwise result in undesirable change of material properties in the vicinity of the seal. This consideration is particularly important in thinner films, e.g., with material thicknesses on the order of 0.05 millimeter, or lower, up to approximately 0.1 millimeter.

Thus, in a continuous process blow extrusion system, wherein the blown film tube is continuously formed into discrete condom articles, the sealing method may be combined with, or otherwise effect, severing of the film into discrete tubular segments for the desired product articles. For example, it may be possible to utilize an ultrasonic sealing assembly comprising an ultrasonic horn having associated therewith a blade element as an integral part of the horn structure, which in combination with a mating anvil effects concurrent or substantially contemporaneous severing of the tubular film into discrete sequential tubular segments and ultrasonic bonding of distal ends thereof to form condom articles.

Alternatively, it may be desirable to sever the tubular blow extruded film to form discrete open-ended tubular main sheath portions, followed by a separate distal end sealing operation.

As discussed hereinabove, the condom articles of the present invention may be formed in various configurations, including tubular cylindrical-type configurations, as well as "baggy"-type configurations, the choice of a specific configuration depending on the particular materials of construction and the intended packaging, storage, and use environments of the condom.

In the tubular cylindrical configuration of the condom illustratively shown in FIGS. 1 and 2 hereof, a reinforcing ring is provided at the periphery of the opening at the proximal end of the condom. The purpose of such reinforcing ring is to provide a manually grippable region for application and removal of the condom to the penis for use, as well as to provide a structure facilitating rolling of the condom when the condom is to be provided to the end user in rolled form, and, to the extent that the reinforcement ring is an elastic and resilient element, to assist in the retention of the condom on the penis of a wearer and to prevent the leakage of seminal fluids from the condom during and subsequent to coital activity.

It will be recognized that in lieu of the reinforcement ring illustratively described, there may be provided at the distal end of the condom any of a variety of other attachment, securement, or retention means, including tapes, adhesive-bearing surfaces, strings or straps attached to the distal end of the condom, etc.

While the condom of the present invention may be devoid of any such proximal attachment, securement, and/or retention means, it generally is preferred in practice to utilize a reinforcement ring at the condom proximal end.

Several approaches may be employed to form such a reinforcing ring at the proximal end of the condom. For example, the sheath material at the open proximal end of the condom may be rolled onto itself, and then tacked in place employing, e.g., a thermal weld or an elastomeric adhesive. Alternatively, the sheath material at the open proximal end of the condom may be rolled onto a ring of a different material from that employed to form the sheath portion of the condom, or it may be rolled onto a ring of the same material, followed by securement of the rolled length of condom to the ring structure. Still another approach is to roll the open end of the condom onto a narrow section of a second piece of the tubular film material, of the same material of construction as the main sheath portion of the condom. It will be appreciated that all such rolling techniques must be carefully controlled during the manufacturing process, to avoid excessive wrinkling of the sheath material at the proximal end, such as otherwise may cause distortion of or undesired reduction in the diametral extent of the proximal opening of the condom.

A still further approach to forming a reinforced proximal opening for the condom article, is simply to fold the open end material back onto the exterior surface of the sheath portion, in the vicinity of the proximal opening. For example, an untacked single fold approximately 0.25 inch wide may be employed.

As discussed hereinabove, condom articles of the present invention are suitably produced by blow forming, i.e., blow molding or blow extrusion forming.

In blow molding, an extruded parison tube of heated thermoplastic is introduced between respective halves of an open split mold, and then expanded against the sides of the closed mold via fluid pressure, typically a volume of interiorly provided air. The mold then is opened and the tubular part ejected. This method is generally economical for and amenable to high volume manufacturing of one piece hollow articles, which may vary considerably in complexity of shape. Blow molding generally requires close attention to and control of processing conditions to obtain highly uniform wall thicknesses in the molded article.

Blow extrusion forming typically involves feeding of a thermoplastic or thermosettable molding compound from a hopper to a screw and barrel, where the molding compound is heated to a plastic state and then urged forwardly, typically by a rotating screw, through a nozzle of a selected cross-sectional configuration. An air bubble is introduced into the interior of the tubular extruded film, and the pressure of such air bubble is employed to control the diametral and film thickness characteristics of the tubular extrudate.

An illustrative blow molding apparatus which may be usefully employed to produce condom articles of the present invention is a Esta blow-molding machine, HS 361 or HS 451, commercially available from Staehle Maschinenbau GmbH, Leinfelden-Echterdingen, Federal Republic of Germany.

Although it may be desirable in some applications of the present invention to utilize thermosetting materials of construction for the condom article, it generally is preferred to utilize thermoplastic materials, most preferably thermoplastic elastomeric materials, although, as indicated, non-elastomeric polymeric materials such as ultra-low density polyethylene or other non-elastomeric homopolymeric or copolymeric films may be advantageously utilized.

When thermoplastic materials are employed to form the tubular main sheath portion of the condom article, and blow extrusion forming is employed, heat sealing methods of closing the distal end of the tubular article to form the condom of the invention are preferred, although any other suitable closure techniques appropriate to the specific materials of construction employed may advantageously be used. When blow molding is employed as the forming method for the condom, no such distal end closure will typically be necessary, since the mold characteristically will be fabricated to form the condom as a unitary, i.e., single piece, product article, having a distal end integrally enclosing the tubular main sheath portion of the condom.

Depending on the specific materials of construction employed, it may be particularly advantageous in some instances to utilize blow extrusion to form the tubular main sheath portion of the condom, due to the ability of blow extrusion to impart biaxial orientation to the formed tubular film. It will be recognized that the specific blow forming techniques which may be usefully employed for a given application may be widely varied, depending on the materials of construction, type of condom configuration desired, processing rates employed, etc.

The features and advantages of the present invention are more fully shown with respect to the following illustrative examples, which, however, are not to be limitingly construed as regards the nature and practice of the present invention.

EXAMPLE I

Based on initial materials selection criteria including tensile strength, elongation, hardness, and flexural modulus, the materials identified in Table I below were selected for testing as materials of construction for condom articles of the present invention. Set out in Table I are the generic types and commercial tradenames of the materials selected, together with their appertaining physical property values for tensile strength, elongation, 300% modulus, Shore A hardness, specific gravity and melt temperature (where applicable).

TABLE I

| Sample | Material | Tensile Strength, psi | Elongation, percent | Modulus 300%, psi | Hardness, Shore A | Specific Gravity | Melt Temp., F |
|---|---|---|---|---|---|---|---|
| 1 | Styrene-Butadiene-Styrene Block Copolymer (Kraton D-2104, Shell) | 1700 | 880 | 200 | 43 | 0.93 | — |

TABLE I-continued

| Sample | Material | Tensile Strength, psi | Elongation, percent | Modulus 300%, psi | Hardness, Shore A | Specific Gravity | Melt Temp., F |
|---|---|---|---|---|---|---|---|
| | Chemical Company) | | | | | | |
| 2 | Styrene-Ethylene/Butylene-Styrene Block Copolymer (Kraton G-2701, Shell Chemical Company) | 1600 | 800 | 480 | 67 | 0.90 | — |
| 3 | Styrene-Ethylene/Butylene-Styrene Block Copolymer (Kraton G-2706, Shell Chemical Company) | 850 | 950 | 130 | 28 | 0.90 | — |
| 4 | Styrene-Ethylene/Butylene-Block Copolymer (KTR-27-G, Shell Chemical Company) | — | — | — | — | — | — |
| 5 | Dispersion of Polypropylene in EPDM Rubber (Santoprene 201-64, Monsanto Company) | 1000 | 400 | — | 64 | 0.97 | 380 |
| 6 | Olefinic Thermoplastic Elastomer (Telcar 81-D-954A, Teknor Apex) | 560 | 740 | — | 45 | 1.18 | 425 |
| 7 | Polybutylene Terephthalate/Polyether Glycol Block Copolymer, Polyester Elastomer (Hytrel 3548, E. I. du Pont de Nemours & Company, Inc.) | — | — | — | D35 | 1.15 | 370 |
| 8 | Polyester Block Amide (Pebax 3533-SN-00, Atochem) | — | — | — | D35 | 1.01 | — |
| 9 | Polyester Block Amide (Pebax 4011-MA-00, Atochem) | — | — | — | — | — | — |
| 10 | Urethane Thermoplastic Elastomer (P3429, J. K. Quinn Co.) | — | — | — | — | — | — |
| 11 | Olefinic Thermoplastic Elastomer (ETA-3131E, Republic Chemical Co.) | 3000 | 550 | — | D70 | 0.91 | — |
| 12 | Olefinic Thermoplastic Elastomer (ETA-4010, Republic Chemical Co.) | 1250 | 500 | — | 87 | 0.91 | — |
| 13 | Olefinic Thermoplastic Elastomer (ETA-5081, Republic Chemical Co.) | 3300 | 650 | — | D60 | 0.90 | — |
| 14 | Urethane Thermoplastic Elastomer (Texin 480-A, Mobay Corporation) | 6000 | 500 | 1700 | 85 | 1.20 | 395 |
| 15 | Urethane Thermoplastic Elastomer (Texin DP7-1014, Mobay Corporation) | 6000 | 675 | 1000 | 83 | 1.12 | — |

The foregoing materials identified in Table I were evaluated for suitability to blow extrusion processing. Crude tubes formed by blow extrusion of these samples then were qualitatively evaluated with respect to their processability and compatibility with the blow extrusion technique.

The blow extrusion apparatus employed in this evaluation was a laboratory-sized unit manufactured by C. W. Brabender Instruments, Inc., (South Hackensack, N.J.) including a Model 3003 extruder and a Model BFW-100 take-off tower. The extruder had a 0.75 inch diameter screw and a 30:1 length to diameter ratio, with three heater zones. An add-on extruder die functioned as a fourth heater zone. The take-off tower effected pulling and conveying of the extruded tube in a vertical direction until it was sufficiently cooled. The top of the take-off tower comprised a set of rolls to collapse the contained air bubble and redirect the tube to a final take-up roll. The take-off tower also comprised controls for air pressure for internal tube pressurization, and controls for external tube cooling.

The extruder die employed for extruding thin, small diameter tubes in this initial qualitative evaluation, was a C. W. Brabender 0.5 inch diameter (outer ring diameter) heated die. An inner die, provided with the unit, measured 0.46 inch, thereby providing an annular gap of 0.02 inch, through which the molten polymer flowed and formed the tube. In initial blow extrusion trials, the formed tubular film was thicker than desired. To achieve a thinner product, the inner die was replaced by a die with a diameter of 0.48 inch, providing a gap of 0.01 inch, which produced desirable tube thicknesses, ranging from 0.0015 to 0.005 inch after blowing, depending on the specific material processed.

Results of the initial qualitative assessment of Samples 1-15 are set out in Table II below.

TABLE II

| Sample | Processability[a] | Properties of Extruded Tube |
|---|---|---|
| 1 | fair | Soft, good elasticity, poor strength in machine direction, |
| 2 | fair | Limited elasticity |
| 3 | good | Soft, good elasticity, behaves similar to latex, tends to stick to itself |
| 4 | poor | Good elasticity, very thick wall, very difficult to get uniform thin bubble |
| 5 | good | Poor strength in both directions, limited elasticity, |
| 6 | poor | Moderate strength, limited elasticity |
| 7 | excellent | Good strength, limited elasticity tendency to stick to itself |
| 8 | good | Tough, reasonable elasticity, good strength, only slight tendency to stick to itself |
| 9 | excellent | Tough, much less elasticity than Sample 8 when dry, soaking in water to take advantage of hydrophilic nature of this polymer increased elasticity with little loss in strength |
| 10 | poor | Very tough, reasonable elasticity, sticks to itself strongly |
| 11 | poor | Very low elasticity, not soft, poor strength |
| 12 | fair | Tough, fair-poor strength, limited elasticity, tendency to stick to itself |
| 13 | poor | Very low elasticity, not soft, poor strength |
| 14 | good | Very tough, good strength, limited elasticity, slight tendency to stick to itself |
| 15 | fair | Very tough, limited elasticity, |

Based on the results shown in Table II, Samples 3 and 4 (styrene-butadiene-styrene block copolymers), Sample 7 (polybutylene terephthalate/polyether glycol block copolymer), Samples 8 and 9 (polyether block amides), and Sample 14 (polyester-based polyurethane) exhibited the best processability/extruded tube properties of the various materials tested. Among the olefinic thermoplastic elastomeric materials tested, significant processing difficulty was encountered, and the resulting blown tubes exhibited generally insufficient elasticity and limited strength, relative to the other materials evaluated.

In addition to the tabulated materials whose processability and extruded tube properties are described in Table II, an ultra-low density polyethylene material (Sample 16; ATTANE ™ 4003 ethylene-octene copolymer, commercially available from The Dow Chemical Company, Midland, Mich.) was evaluated. This polymeric material is not an elastomeric thermoplastic, however it was very easy to process via blow extrusion and produced tube samples in the desired range of diameter and thickness. This ultra-low density polyethylene was not as soft as some of the other materials, such as the styrene-butadiene-styrene block copolymer of Sample 3, and did not recover from high strain extensions, but was relatively extensible.

EXAMPLE II

On the basis of the results obtained in Example I, a further blow extrusion evaluation was carried out for Samples 3, 4, 7, 8, 9, 14, and 16, using refined operating parameters.

In contrast to the initial extrusion evaluation of Example I wherein the inner die had a diameter of 0.46 inch, the further extrusion tests employed an inner die having a diameter of 0.48 inch.

Of the aforementioned seven selected material samples (Samples 3, 4, 7, 8, 9, 14 and 16), Samples 4 and 8 were undesirably difficult to process in low film thicknesses. Specifically, Sample 4 did not stabilize in a thin blown bubble, and Sample 8 exhibited an undesirable tendency to self-adhere, even with extended cooling. The remaining five samples, Samples 3, 7, 8, 9, 14 and 16, produced extruded tube diameters and film thicknesses which were much closer to the desired values.

Table III below provides a summary of processing conditions for the blow extrusion processing of these samples, together with the approximate thickness range, in inches, achieved for each of the blow extruded samples.

TABLE III

| Sample | Extruder Temperature | | | | Extruder Speed, RPM | Blow Pressure, Oz/sq. in. | Cooling Pressure, psi | Approximate thickness range, inch |
|---|---|---|---|---|---|---|---|---|
| | zone 1 | zone 2 | zone 3 | zone 4 | | | | |
| 3 | 300 | 340 | 370 | 380 | 7 | 8 | 11 | 0.0050–0.0055 |
| 7 | 320 | 375 | 380 | 380 | 7 | 1–8 | 15 | 0.0030–0.0040 |
| 8 | 360 | 370 | 380 | 400 | 7 | 12 | 10 | — |
| 9 | 400 | 410 | 430 | 450 | 4 | 2 | 13 | 0.0025–0.0035 |
| 14 | 300 | 330 | 360 | 380 | 6 | 3 | 10 | 0.0015–0.0025 |
| 16 | 400 | 430 | 440 | 450 | 4 | 2 | 10 | 0.0020–0.0025 |

EXAMPLE III

In this test, blow extruded tubes produced in Example II were evaluated for heat sealing capability, utilizing heat sealing as a method for forming a closed distal end of the tube for condom usage. Extruded tubes of Samples 3, 7, 9, 14, and 16 were evaluated.

In a preliminary evaluation, a laboratory thermal impulse heat sealer, commercially available from Vertrod, Inc., was employed.

The impulse heat sealer is a potentially attractive means for forming enclosed distal ends on blow extruded tubes for condoms of the present invention, because it can initiate the sealing process at a low temperature, with the material to be sealed quickly rising to the desired elevated sealing temperature, and then returning quickly to ambient conditions. The resulting rapid sealing in a localized region prevents surrounding material in the vicinity of the seal from experiencing undesirable temperature changes such as may deleteriously alter material properties. Such localized heating character is particularly important in thin film sealing applications such as forming enclosed distal ends for blow extruded condoms of the present invention.

In application of the thermal impulse heat sealer to the aforementioned extruded tubes, Samples 14 and 16 were heat sealed effectively at moderate power levels, with the resulting heat seals being strong, effective, soft, and easily trimmed. Samples 3, 7, and 9, by contrast, were unable to be effectively sealed with the impulse heat sealer even at higher power levels and longer dwell times.

In a second phase of the sealing evaluation, a conventional melt heat seal was employed to form a closed end on the extruded tubes. A laboratory thermal heat sealer (Model 18 PR, commercially available from PAC), was modified to form by melt sealing a closed and rounded condom end, i.e., to provide a seal of a semicircular shape (in edge profile) rather than a straight strip. For this purpose, an aluminum heating platen was constructed having a concave hemispherical cavity for sealingly forming rounded ends on the extruded tubes. During heat sealing, the extruded tubes were placed in the hemispherical concave region of the platen and pressed against a hard rubber backup strip to form the seal.

Table IV below sets forth the heat sealing temperatures and dwell times employed for heat sealing each of the identified extruded tube samples.

TABLE IV

| Sample | Temperature, F | Dwell Time, seconds |
| --- | --- | --- |
| 3 | 190 | 3 |
| 7 | 260 | 1 |
| 9 | 340 | 1 |
| 14 | 260 | 1 |
| 16 | 340 | 1 |

EXAMPLE IV

In this example, samples of the blown extruded films (Samples 3, 7, 9, 14, and 16) were tested to compare the properties of condoms according to the present invention to those of conventional latex rubber condoms.

The tests conducted were determinations of ultimate tensile strength, ultimate elongation, 100% modulus, and puncture resistance.

The ultimate tensile strength and ultimate elongation values were measured at material breaking points. The 100% modulus was the force required to stretch the condom to twice its original length.

The puncture resistance test simulated a fingernail and finger being pushed through a condom, and comprised a lower base unit which clamped and secured the condom film, providing a circular opening of 1 inch diameter within which the clamped film was exposed. A finger simulator probe was pushed through the base unit opening and into the film using an Instron test unit which monitored the probe travel and the force applied to the probe. The probe comprised a 0.5 inch diameter steel rod tapered at its end to a central wedge shape with a thickness of 0.025 inch, and rounded at its extremity to a radius of curvature of 0.25 inch. After the puncture tests were conducted and the load to puncture recorded, the data were normalized based on the thickness of each material sample. This resulted in final puncture data in units of force to puncture per unit thickness (pounds per inch).

From six to eight measurements were taken for each sample in determining the tensile strength, percent elongation, and 100% modulus values; from three to five measurements were taken for each sample to determine puncture resistance. Mean measurement values were determined in each of the test procedures, for each sample tested, and the results are set out in Table V below.

The data for Samples 3, 7, 9, 14, and 16 are shown together with data for a control film of conventional latex condom material, for comparison purposes.

TABLE V

| Sample | Sample Thickness, inches | Tensile Strength, psi | Percent Elongation | 100% Modulus, psi | Load to Puncture lbs/inch |
| --- | --- | --- | --- | --- | --- |
| 3 | 0.0055 | 811 | 1241 | 83 | 503 |
| 7 | 0.0048 | 1386 | 993 | 604 | 587 |
| 9 | 0.0032 | 434 | 204 | 415 | 207 |
| 14 | 0.0028 | 5193 | 863 | 772 | 1104 |
| 16 | 0.0021 | 1793 | 781 | 990 | 1253 |
| Control | 0.0030 | 1656 | 1163 | 123 | 928[a] |

[a] 925 minimum level, likely to be higher

The polyester-based polyurethane film (Sample 14) provided the highest tensile strength at 5193 psi. The next highest tensile strength material was the ultra-low density polyethylene film (Sample 16) at 1800 psi and the conventional latex condom film (control) at 1665 psi. The lowest strength material was the polyester block amide material (Sample 9) at 434 psi; this material was tested after soaking it in water for a minimum of 24 hours to reduce its stiffness.

The conventional latex rubber material (control) and the styrene-butadiene-styrene block copolymer (Sample 3) showed comparable elongation characteristics (1163% for the control, and 1241% for Sample 3). The polyester block amide material (Sample 9) had the lowest elongation at 204%, while the remaining three materials exhibited between 800% and 1000% elongation.

The lowest, and most desirable, 100% modulus value was obtained with the styrene-butadiene-styrene block copolymer material (Sample 3) at 83 psi. The control had a 100% modulus value of 123 psi. The remaining materials required much higher stress levels to stretch them to twice their original length. The highest 100% modulus level was obtained for the ultra-low density polyethylene material (Sample 16) at 990 psi, and the polyester-based polyurethane (Sample 14) was also relatively high at 772 psi.

With regard to puncture resistance, the materials tested fell into two general classes. The ultra low density polyethylene (Sample 16), the polyester-based polyurethane (Sample 14) and the latex rubber material (control) required high loads to initiate a puncture. The remaining materials (Samples 3, 7, and 9) [Note: Sample 9 was tested wet in the puncture test], exhibited punctures at loads which were approximately one-half of the loads necessary to initiate puncture in the first-mentioned class of materials.

While the invention has been described with reference to particular examples and embodiments, it will be apparent that numerous variations, alternatives, and modifications are possible, and accordingly all such variations, alternatives, and modifications are to be regarded as being within the spirit and scope of the present invention.

What is claimed is:

1. A method of making a tubular condom article, comprising:
    extruding a tubular film of a thermoplastic elastomeric film material;
    interiorly pressurizing the extruded tubular film at a pressure of from 1 to 12 ounces per square inch of film, to form an expanded tubular film constituting a tubular main sheath portion of the condom having respective first and second ends, which has a film thickness of from 0.0015 inch to 0.005 inch and which is of a size and character permitting the condom to be closely conformable to a penis of a wearer;

sealing the first end of the tubular main sheath portion to form a closed distal end for the condom whereby the condom comprises the tubular main portion with the closed distal end and an open proximal end; and providing a reinforcing ring at the periphery of the open proximal end of the tubular main sheath portion.

2. A method according to claim 1, wherein the tubular main sheath portion has film thickness of from 0.002 inch to 0.004 inch.

3. A method according to claim 1, wherein the extruding step is conducted at temperature in the range of from about 300° F. to about 450° F.

4. A method according to claim 1, wherein said sealing step comprises heat sealing the first end of the tubular main sheath portion.

5. A method according to claim 1, wherein the sealing step comprises impulse heat sealing the first end of the tubular main sheath portion.

6. A method according to claim 5, wherein said impulse heat sealing is conducted at temperature in the range of from 190° F. to 340° F.

7. A method according to claim 6, wherein the impulse heat sealing is carried out at said temperature for a period of from 1 to 3 seconds.

8. A method according to claim 1, wherein said sealing comprises ultrasonic sealing of the first end of the tubular main sheath portion.

9. A method according to claim 8, wherein said ultrasonic sealing is carried out with contemporaneous severing of the expanded tubular film.

10. A method according to claim 1, wherein said thermoplastic elastomeric film material comprises a material selected from the group consisting of: polyurethane materials; polyester elastomers; polyether block amides; multiblock rubber-based copolymers; and copolymers, mixtures, alloys and composites thereof.

11. A method according to claim 1, wherein the thermoplastic elastomeric film material comprises a material selected from the group consisting of polyester-based polyurethanes and multiblock rubber-based copolymers.

12. A method according to claim 1, wherein the thermoplastic elastomeric film material comprises polyurethane.

13. A method according to claim 1, wherein the thermoplastic elastomeric film material comprises polyurethane having: a specific gravity of from about 1.15 to about 1.25; a Shore A hardness of from about 80 to about 95; a break tensile stress of from about 4500 to about 6,000 psi; a tensile stress at 50% elongation of from about 720 to about 2400 psi; an ultimate elongation of from about 450% to about 600%; a flexural modulus of from about 4,000 to about 37,000 psi; and a tear strength from about 500 to about 1,000 pli.

14. A method according to claim 1, wherein the thermoplastic elastomeric film material comprises a multiblock rubber-based copolymer having: a Shore A hardness of from about 25 to about 100; a tensile strength of from about 500 to about 4500 psi; a 300% modulus of from about 120 to about 1,000 psi; and an ultimate elongation of from about 200% to about 1400%.

* * * * *

UNITED STATES PATENT AND TRADEMARK OFFICE
CERTIFICATE OF CORRECTION

PATENT NO.   : 5,169,464
DATED        : December 8, 1992
INVENTOR(S)  : Robin G. Foldesy, et al.

It is certified that error appears in the above-indentified patent and that said Letters Patent is hereby corrected as shown below:

At column 1, prior to the first line of text, insert:

-- GOVERNMENT LICENSE RIGHTS

The invention claimed herein was made under one or more of the following contracts:  U.S. Agency for International Development Contract Nos. DPE-3041-A-00-0043 and DPE-0537-A-00-4047, and National Institutes of Heal Contract No. N01-HD-2-3143, and the U.S. Government has certain rights therein. --

Signed and Sealed this

Eighth Day of April, 1997

Attest:

BRUCE LEHMAN

Attesting Officer

Commissioner of Patents and Trademarks